(12) United States Patent
Baird et al.

(10) Patent No.: US 6,619,961 B2
(45) Date of Patent: Sep. 16, 2003

(54) COMPUTERIZED SYSTEM AND METHOD FOR SIMULTANEOUSLY REPRESENTING AND RECORDING DYNAMIC JUDGMENTS

(76) Inventors: John Charlton Baird, 456 Cornish Turnpike, Newport, NH (US) 03773; Marek Cezary Chawarski, 350 Willow St., New Haven, CT (US) 06511

( * ) Notice: Subject to any disclaimer, the term of this patent is extended or adjusted under 35 U.S.C. 154(b) by 0 days.

(21) Appl. No.: 10/016,623

(22) Filed: Dec. 10, 2001

(65) Prior Publication Data

US 2002/0119431 A1 Aug. 29, 2002

Related U.S. Application Data

(60) Provisional application No. 60/270,854, filed on Feb. 23, 2001, and provisional application No. 60/292,115, filed on May 18, 2001.

(51) Int. Cl.$^7$ .............................................. G09B 19/00
(52) U.S. Cl. ...................................... 434/236; 434/238
(58) Field of Search ................................ 434/236, 237, 434/238

(56) References Cited

U.S. PATENT DOCUMENTS

| | | | | |
|---|---|---|---|---|
| 4,671,772 A | * | 6/1987 | Slade et al. ................. | 434/219 |
| 5,882,203 A | * | 3/1999 | Correa et al. ............... | 434/236 |
| 6,007,340 A | * | 12/1999 | Morrel-Samuels .......... | 434/236 |
| 6,405,159 B2 | * | 6/2002 | Bushey et al. ............... | 703/13 |

OTHER PUBLICATIONS

John Baird et al.; Student Planning of Town Configuration; Jun., 1972; pp. 159–188; Student Town Planning.

Jill Nagy et al.; Children as Environmental Planners; 1978; pp. 259–294; Children and the Environment.

John Baird; Studies of the Cognitive Representation of Spatial Relations: I. Overview; 1979; pp. 90–91; Journal of Experimental Psychology: General, vol. 108, No. 1.

John Baird; Studies of the Cognitive Representation of Spatial Relations: II. A Familiar Environment; 1979; pp. 92–98; Journal of Experimental Psychology: General, vol. 108, No. 1.

John Baird et al.; Studies of the Cognitive Representation of Spatial Relations: III. A Hypothetical Environment; 1979; pp. 99–106; Journal of Experimental Psychology: General, vol. 108, No. 1.

Peter Engeldrum et al.; Some Experiments on the Perception of Graininess of Black and White Photographic Prints; Jan./Feb. 1985; pp. 18–23; Journal of Imaging Science, vol. 29, No. 1.

Peter Engeldrum, Print–Quality Requirements; 1991; pp. 141–144; Proceedings of the SID, vol. 32/2.

* cited by examiner

*Primary Examiner*—John Edmund Rovnak
(74) *Attorney, Agent, or Firm*—Devine, Millimet & Branch, PA; Kevin J. Carroll, Esq.

(57) ABSTRACT

The computerized system and method represents judgments of a user and records the judgments and the judgment making process. In one embodiment, the computerized method displays multiple concept representations simultaneously, receives a user-manipulated adjustment to one or more of the concept representations to create a judgment representation, and records the judgment representation(s) and user-manipulated adjustment(s). The judgment representations and adjustments are preferably recorded continuously so that the judgment process can be reviewed and evaluated. The concept representations can be displayed relative to other concept representations and/or relative to a rating scale. In another embodiment, the computerized method displays a physical context representation and the judgments are represented and recorded as user designated locations in the physical context. One example of an application for the system and method is to record and evaluate a patient's judgments with respect to pain.

13 Claims, 15 Drawing Sheets

SAMPLE RESULTS FROM DYNAMIC SCALING IN POLAR COORDINATES

PASTA
RICE
POTATOES

BROCCOLI
RED MEAT    FISH    GREEN BEANS
CHICKEN                            ← 60

LETTUCE

SODA
MILK    WATER

FIG. 20

COMPUTERIZED SYSTEM AND METHOD FOR SIMULTANEOUSLY REPRESENTING AND RECORDING DYNAMIC JUDGMENTS

CROSS REFERENCE TO RELATED APPLICATIONS

The present application claims the benefit of U.S. Provisional Application Ser. No. 60/270,854, filed Feb. 23, 2001, and U.S. Provisional Application Ser. No. 60/292,115, filed May 18, 2001, both of which are fully incorporated herein by reference.

STATEMENT REGARDING FEDERALLY SPONSORED RESEARCH OR DEVELOPMENT

This invention was made with Government support under SBIR grant Nos. 1 R43 MH62833-01, 1 R43 NS42387-01, 1 R43 HL/MH68493-01 awarded by the National Institutes of Health. The Government has certain rights in the invention.

TECHNICAL FIELD

The present invention relates to methods for representing and recording personal judgments and more particularly, relates to a computerized system and method for representing and recording dynamic, relative judgments of physical or non-physical concepts in one or two dimensions.

BACKGROUND INFORMATION

Studies have been performed using cognitive mapping methods to assess a person's conception of the perceived or ideal distances between actual or hypothetical physical objects, such as buildings on a campus or in a town, or the perceived glossiness of images in a photograph. These studies have been done both by physical manipulation of objects (photographic prints), as well as by using a computer system to record the location of objects placed by an individual in a grid appearing on a computer monitor. These studies and methods are described in various publications[1], all of which are incorporated herein by reference.

Baird, J. C., Degerman, R., Paris, R. & Noma, E. (1972). Student planning of town configuration. *Environment and Behavior*, 4, 159–188. Nagy, A. N. and Baird, J. C. (1978). Children as environmental planners. Chapter in Altman, I. and Wohlwill, J. F. (Eds.) *Children and the Environment*, Plenum Press, New York, pp. 259–294. Baird, J. C. (1979). cognitive representation of spatial relations: I. Overview. *Journal of Experimental Psychology: General*, 108, 90–91. Baird, J. C., Merrill, A. A. and Tannenbaum, J. (1979). Cognitive representation of spatial relations: II. A familiar environment. *Journal of Experimental Psychology: General*, 108, 92–98. Merrill, A. A. and Baird, J. C. (1979). cognitive representation of spatial relations: III. A hypothetical environment. *Journal of Experimental Psychology: General*, 108, 99–106. Engeldrum, P., & McNeill, G. (1985). some experiments on the perception of graininess in black and white prints. Journal of Image Science, 29, 18. Engeldrum, P. (1991). *Print-Quality Requirements*, Proceedings of SID, 32, One problem with the methods described in these publications is that they have only been used to scale judgments of objects that are naturally situated in a metric space (buildings) or of physical stimuli that are directly perceived by an observer (photographic prints). These methods are also limited in that they do not provide a precise measure of the rating assigned to each item, because the location of the item along the scale has an error bar equal to the width of the pictorial word or icon. These methods also are limited in that they do not allow for (e.g., in the case of prints), or have not recorded (e.g., in the case of computer methods) dynamic changes of judgments over time.

Accordingly, a computerized system and method is needed that represents and records the scale values resulting from the dynamic adjustment of the location of multiple concepts in one or two dimensions. A computerized system and method is also needed that allows the user's judgment decisions to be evaluated continuously by recording the changes made in the user's judgments over time.

SUMMARY

To address the needs described above, a computerized system and method is provided for representing judgments of a user, for recording relative judgments in one or two dimensions, and for recording the judgment making process. In general, the computerized method displays multiple concept representations simultaneously, receives a user-manipulated adjustment to one or more of the concept representations to create a judgment representation, and records the judgment representation(s) and user-manipulated adjustment(s). The judgment representations and adjustments are preferably recorded continuously so that the judgment process can be reviewed and evaluated.

In accordance with one aspect of the present invention, the computerized method represents and records relative judgments within a physical context.

In accordance with another aspect of the present invention, the computerized method represents and records relative judgments along a one-dimensional scale.

In accordance with a further aspect of the present invention, the computerized method represents and records relative judgments along a two-dimensional scale.

In accordance with a further aspect of the present invention, the computerized method represents and records relative judgments using a polar coordinate scale.

In accordance with a further aspect of the present invention, the computerized method represents and records relative judgments by associating concepts without any physical context or scale.

In accordance with yet another aspect of the present invention, the computerized method represents and records relative judgments using the above methods together with a fixed resource technique.

The computerized system preferably implements the methods defined above using software and a computing device.

BRIEF DESCRIPTION OF THE DRAWINGS

FIG. 20 is a graphical illustration of concept representations associated in space, according to one example.

DETAILED DESCRIPTION OF THE PREFERRED EMBODIMENTS

Figure 1:
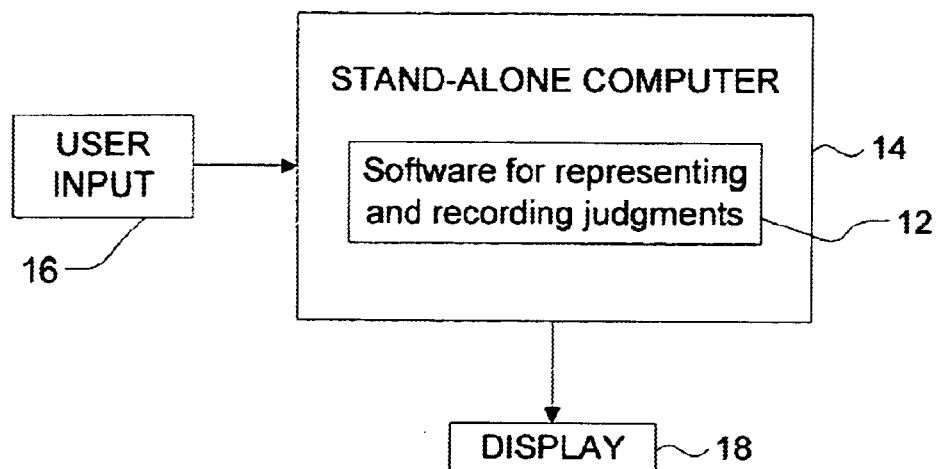
FIGS. 1 and 2 are schematic block diagrams of the computerized system for representing and recording judgments, according to different embodiments of the present invention.
Figure 2:
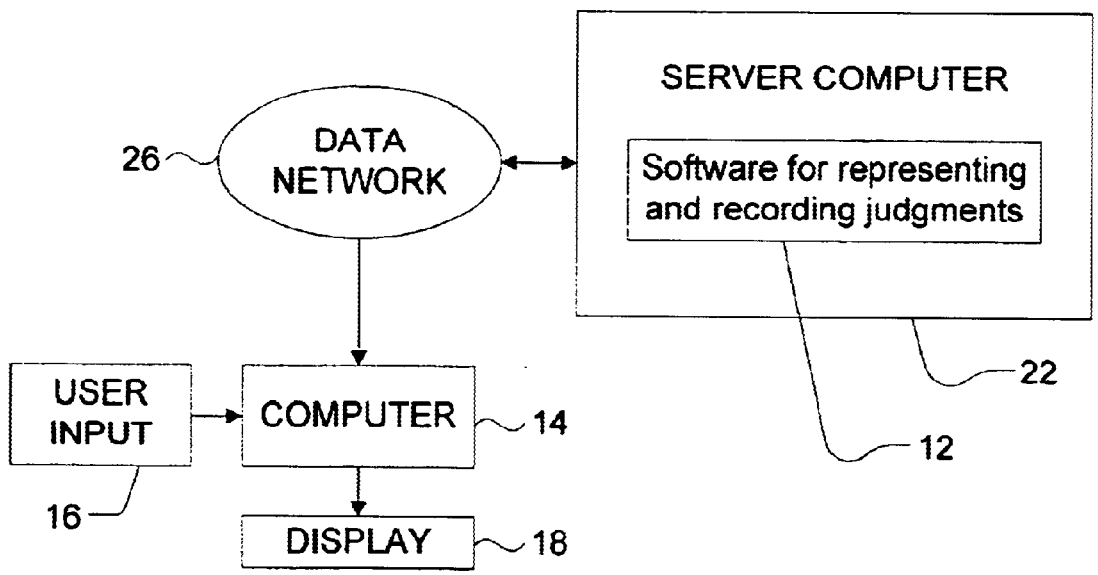

The computerized system for representing and recording judgments, as shown in FIGS. 1 and 2, is preferably implemented using software 12 and a computing device 14 having a user input 16 and a display 18. In one embodiment, the software 12 resides on a stand-alone general-purpose computer 14 (FIG. 1), such as a PC, which is used by the user to access the software 12. In another example, the software 12 resides on a server computer 22 (FIG. 2) and is accessed by the user using a computer 14 connected to the server computer 22 over a data network 26, such as the Internet. The display 18 preferably includes a computer screen or any other similar visual display device known to one skilled in the art. The user input 16 preferably includes a mouse, keyboard, or any other input device known to one skilled in the art.

The software 12 can be implemented to perform the methods described below using programming techniques known to a programmer of ordinary skill in the art. For example, the software 12 on the stand-alone computer 14 can be developed using a programming language such as Basic, and the software 12 residing on the server computer 22 can be developed using a programming language such as Java.

In general, the system displays a two-dimensional space within which one can locate concepts represented by words, pictures or some other icon (such as a solid geometric figure) The concepts can be any physical item (e.g., food) or non-physical concept (e.g., feelings or issues) about which a user can express judgment. Using the user input 16 (e.g., by depressing the mouse button), the user represents one or more relative judgments by locating concept representations in the space relative to other concept representations, a physical context, and/or a scale. The system can receive user-manipulated adjustments of the concept representations relative to each other, the physical context, and/or the scale. In response to the user's manipulation of the concept representation(s), the system draws the concept representation at its user-designated location, such as occurs when icons are moved across the screen in computer operating systems.

The system thus allows the users to dynamically express and/or modify their relative judgments, for example, by positioning the concept representations relative to one another, relative to a scale, and/or relative to a physical context on the computer screen. The sequential order and value of each manipulation and adjustment is recorded, together with the time required by the user to make the adjustment. The user continues locating concept representations on the screen or continues making adjustments of all concept representations until satisfied with the judgments represented. When the user is satisfied, the user signals (e.g., by pressing any key on the computer keyboard), and the system then records the final values of the judgment representations. Various methods of the present invention are described in greater detail below.

Figure 3:
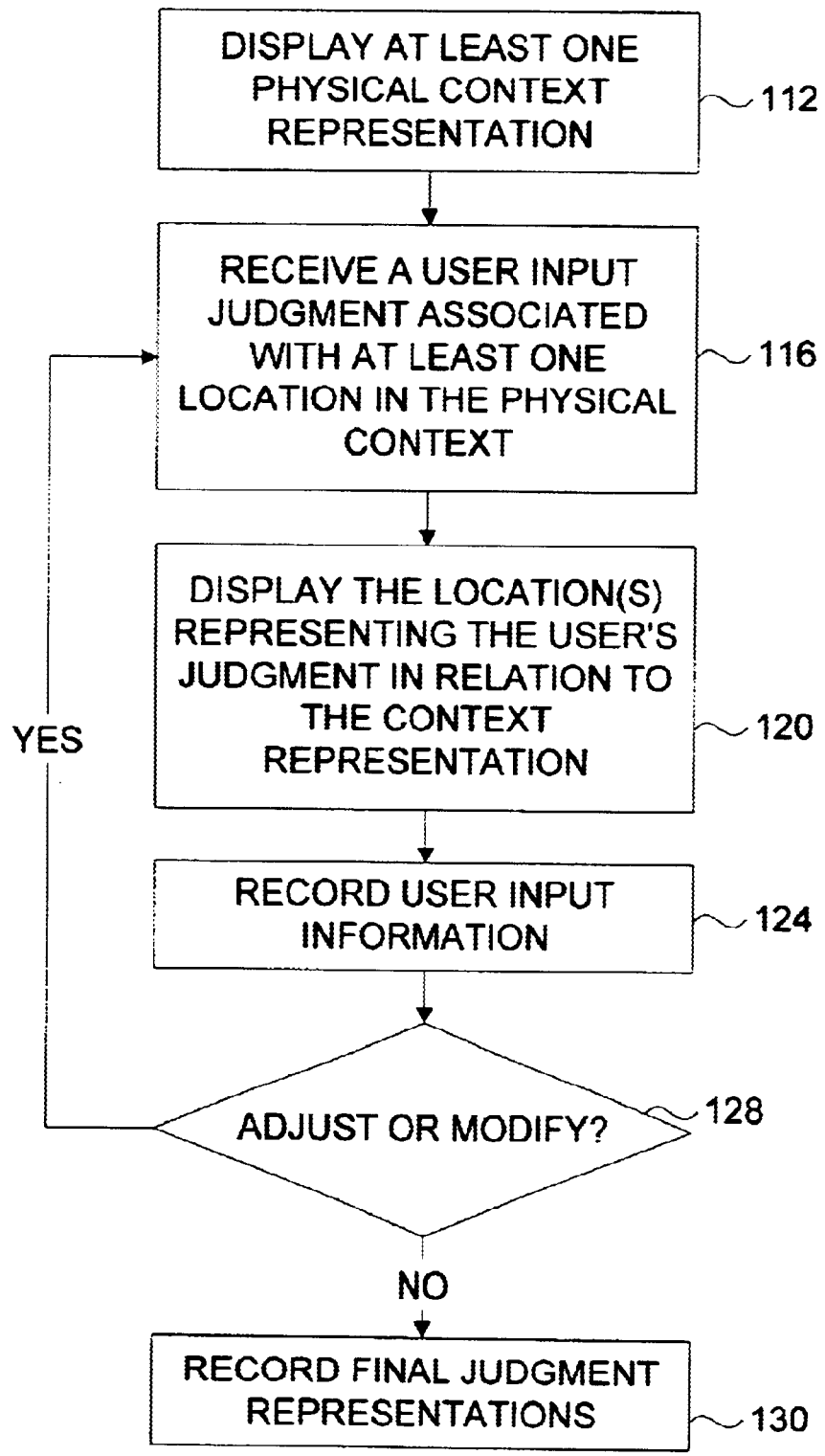
FIG. 3 is a flow chart illustrating a method for representing and recording judgments in a physical context, according to one embodiment of the present invention.

One method of representing and recording judgments in relation to a physical context is illustrated in FIG. 3. According to this method, at least one physical context representation is displayed, step 112. The physical context representation represents the physical context (e.g., the user's body) in which the user is making judgments, and the user is asked to make a judgment by designating locations (e.g., a pain location) in the physical context. The system then receives the user input judgment associated with at least one location in the physical context, step 116. The location representing the user's judgment is then displayed in relation to the physical context representation, step 120. User input information (e.g., each user designation and the time between designations) is recorded as each of the locations are designated by the user, step 124. The user can adjust or modify the judgment representations, step 128, for example, by designating new locations and/or erasing existing designations. The user input information for these adjustments is also recorded. When the user is finished, the final judgment representations are recorded, step 130.

Figure 4:
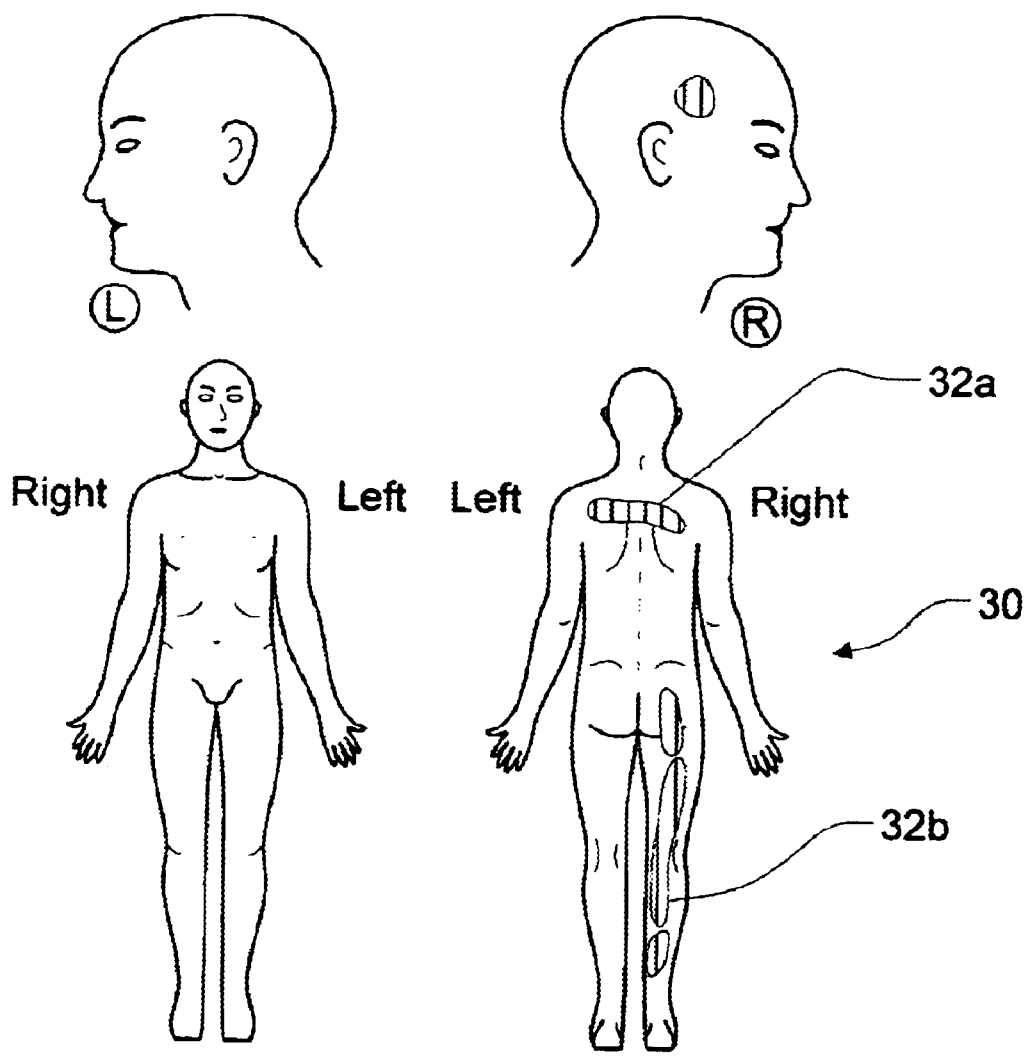
FIGS. 4, 4A and 5 are illustrations of a human form for indicating pain locations, according to one example of the method for representing and recording judgments in a physical context.

Referring to FIG. 4, one example of the method of representing and recording judgments in relation to a physical context is described in greater detail. According to this exemplary method, the user is a patient experiencing a sensory symptom such as pain or itchiness, the physical context is the patient's body, and judgments pertaining to the location of the symptom are recorded. The system displays outline drawings 30 of a human head and body, and the user locates the cursor at one or more locations 32a, 32b on the figure to indicate the pain or itchiness or some other sensory symptom.

Figure 4A:
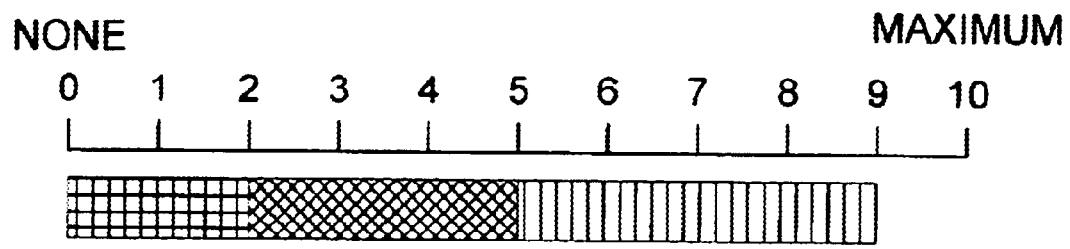
Figure 4A:
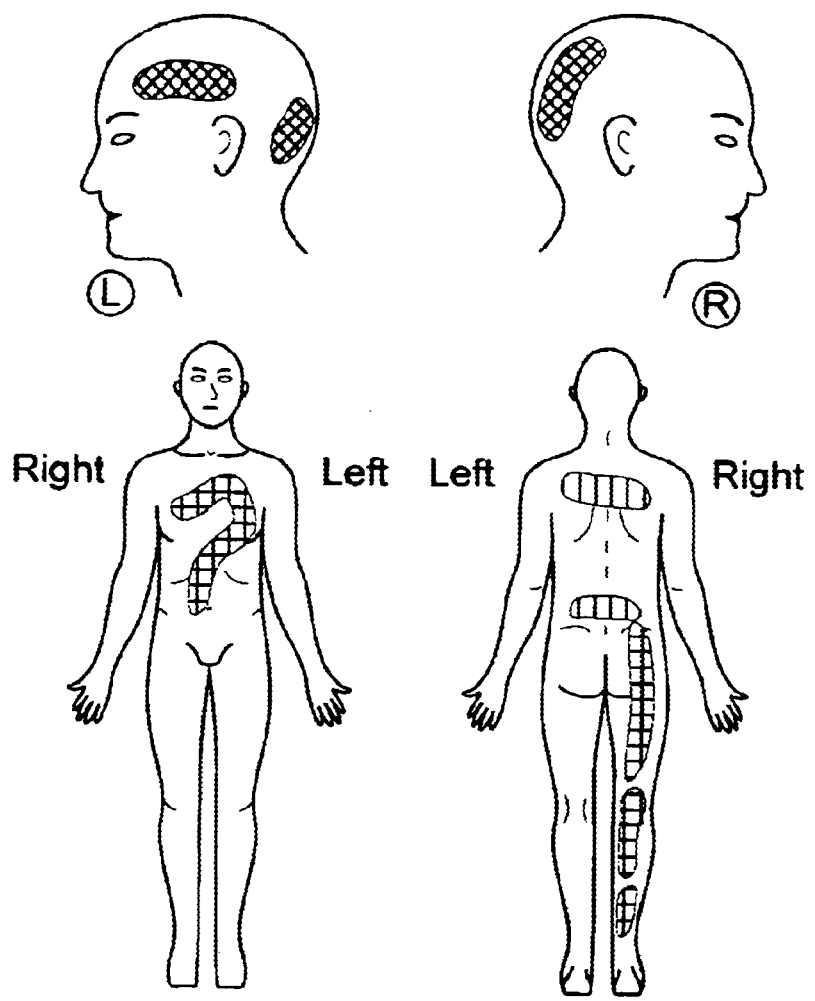

Depressing the mouse results in the appearance of a solid figure (square, circle, or some other geometric figure) at that location. The size of the figure can be adjusted to accommodate the size of the entire drawing as it appears on the computer screen. By holding down the mouse button and moving the cursor, the user can fill in a region on the drawing or indicate the exact pattern of locations on the body where the symptom is experienced. The system preferably only places points that do not overlap with adjacent points so that the system does not have multiple records of the same (or almost the same) placement location. A library of "legal" points (i.e., those falling within the confines of the figure) can be stored separately, and checked by the software before displaying a point indicated by the user. The user can also erase any inadvertent designations. Different colors or types of geometric figures can be used to represent different types of sensory symptoms (e.g., different types or intensities of pain) in a physical context. In one example shown in FIG. 4A, patients can record their symptoms at different intensities on the body picture using different colors to represent the different intensities (as indicated by the scale), thereby providing a symptom scanning technique.

The system records the order of each point's placement on the drawing, for example, by recording the x,y coordinates of each point placed on the drawing. The system also records the times between each designation of a point on the drawing. This data allows an investigator to exactly reproduce the judgment process employed by the user in marking locations on the figure. The recorded judgment data and judgment process data can thus be used to evaluate the patient's condition. In one example, an animated graphical representation showing the judgment process can be replayed (e.g., as a movie) to visualize the exact manner in which the user made each judgment. In another example, the data can be compared to previously recorded data for other patients, which has been stored in a library of data, to give a likely diagnosis for consideration by the physician.

Figure 5:
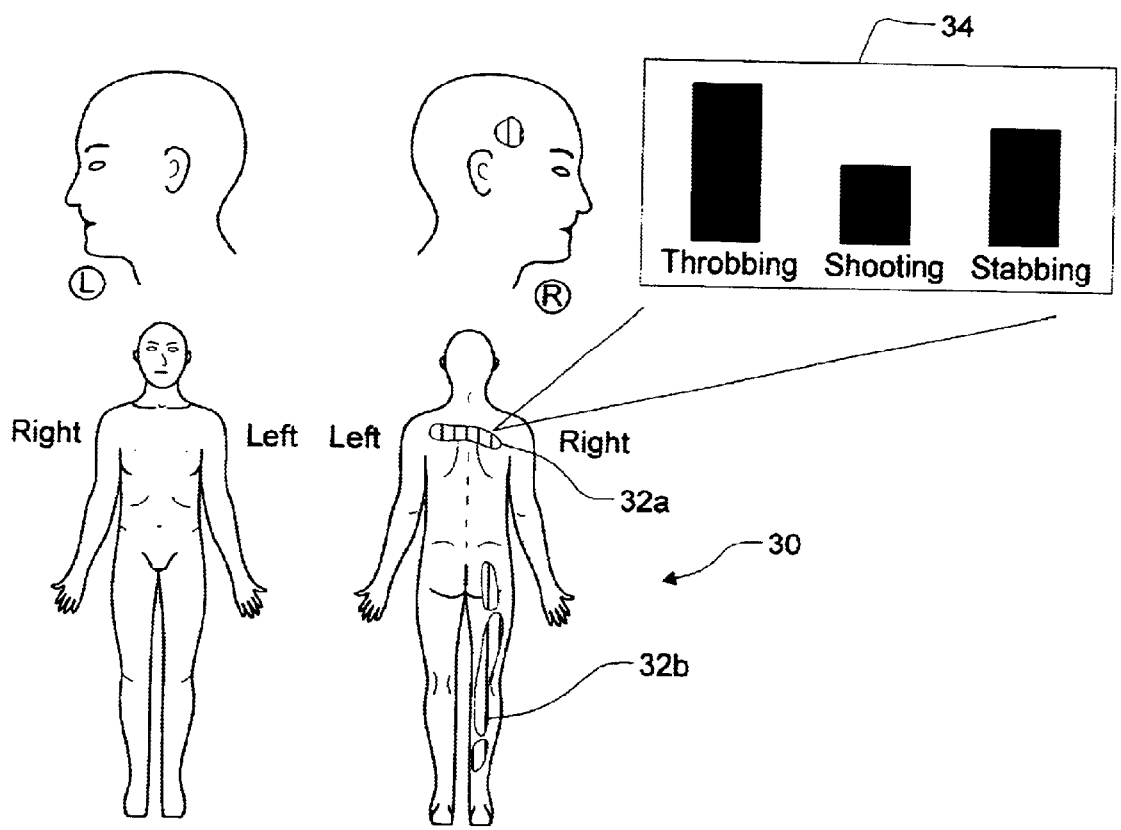

According to one variation of this method for representing and recording judgments of sensory symptoms, as shown in FIG. 5, multidimensional judgments pertaining to the symptoms at each user-designated location can be represented and recorded. For example, a graphical representation 34 associated with a user-designated location can be displayed to allow the user to make the multidimensional judgments further characterizing the symptoms. Examples of methods for representing and recording multi-dimensional judgment representations (e.g., using a fixed resource technique) are described in greater detail in co-pending provisional application Serial No. 60/270,854 (Attorney Docket No. BAIRD-001PR) and application Ser. No. 09/950,126 (Attorney Docket No. BAIRD-001XX), both of which are incorporated herein by reference. Other methods for representing and recording judgments to further characterize the symptoms include the methods described in greater detail below.

Figure 6:
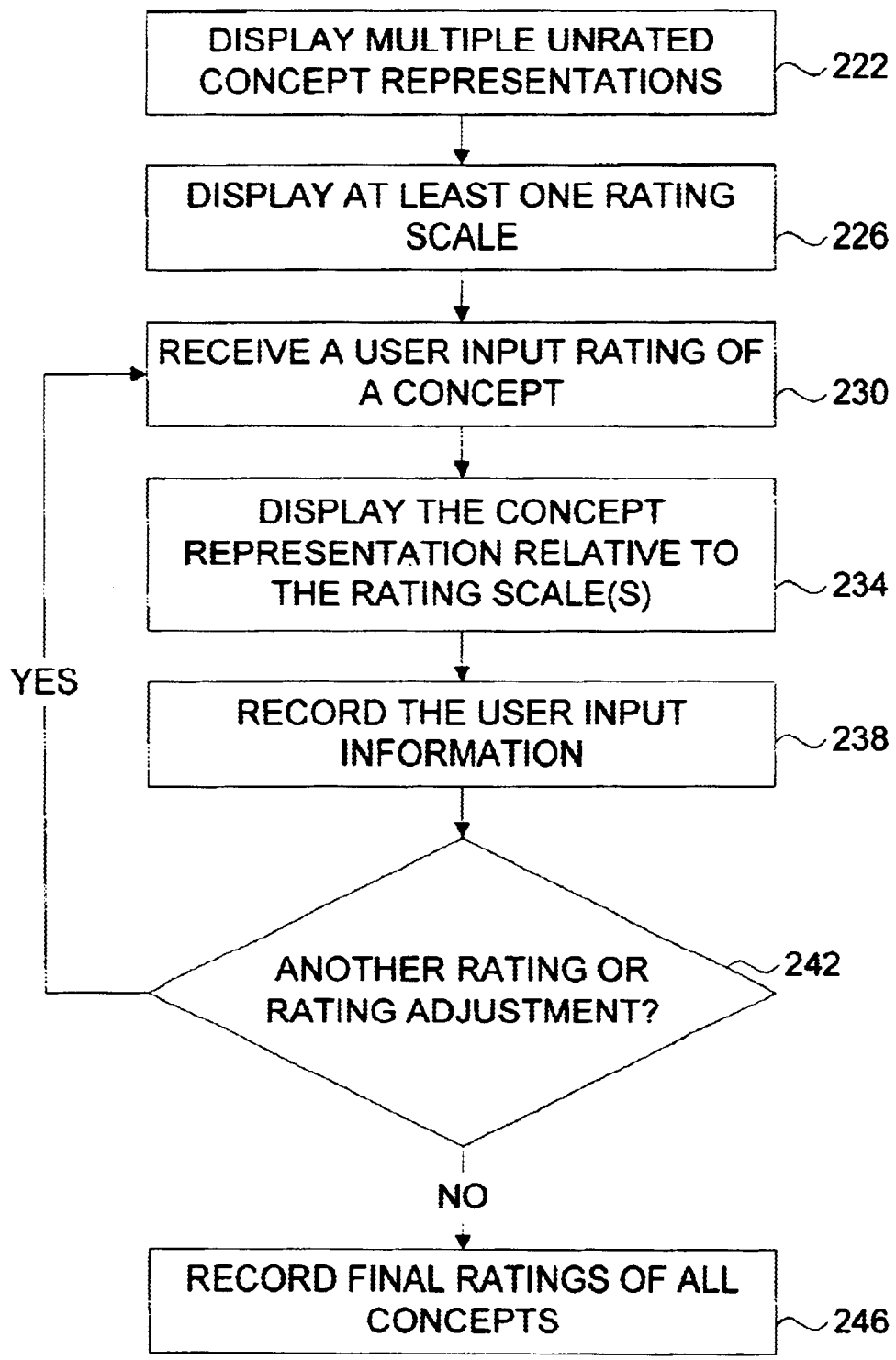
FIG. 6 is a flow chart illustrating a method for representing and recording judgments in relation to a rating scale, according to another embodiment of the present invention.
Figure 7:
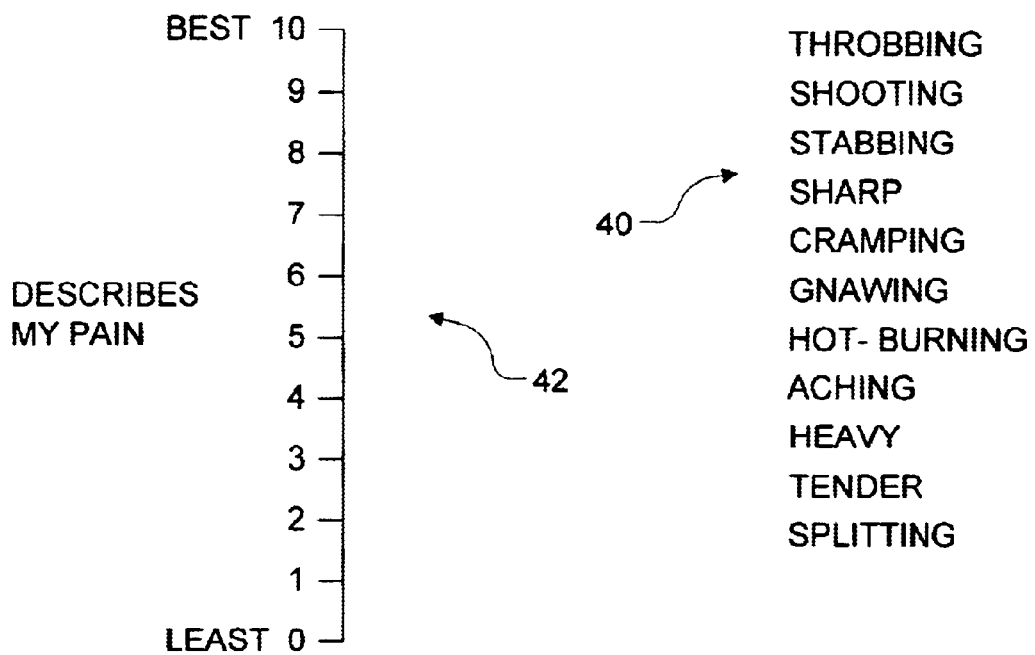
FIG. 7 is a graphical illustration of a vertical rating scale with unrated concept representations corresponding to various types of pain, according to one example of the method for representing and recording judgments in relation to a rating scale.

One method of representing and recording judgments in relation to a rating scale is illustrated in FIG. 6. According to this method, multiple unrated concept representations are displayed (e.g., using words, pictures or icons), step 222. The concepts can be physical or non-physical and can include anything about which a user can express a judgment. One or more rating scales are also displayed, step 226. The rating scale(s) provide a range of possible judgments applicable to the concepts (e.g., degrees of pain). The user is asked to make a judgment rating each of the concepts in relation to the rating scale(s) and in relation to one another, for example, by manipulating and locating the concept representations along the rating scale(s). When the user input rating of a concept is received, step 230, the concept representation is displayed in relation to the scale, step 234. User input information is recorded as the user rates (or adjusts the rating of) each of the concepts, step 238. If the user wants to rate another concept or adjust a rating, step 242, these steps are repeated. When the user is satisfied, the final ratings are recorded as the user's judgment representation, step 246.

Referring to FIGS. 7–17, examples of the method of representing and recording judgments in relation to a rating scale are described in greater detail. As shown by example in FIG. 7, words initially appear in a vertical list 40 on the screen and a single linear scale 42 appears on the screen with numerical values (e.g., integers 1 to 10) and tick marks. The scale 42 can be oriented either vertically (FIGS. 7–10) or horizontally (FIGS. 11–15). The user moves the words (i.e., the concept representations) to positions along the scale 42 to indicate an amount or degree along the dimension, thereby representing the user's judgment by rating the concept. In one example, the movement is accomplished by positioning the cursor on the word, clicking on the mouse, and moving the cursor. The system automatically erases the old representation of the word and draws it in the new location. This occurs continuously as the cursor is moved.

Figure 15:
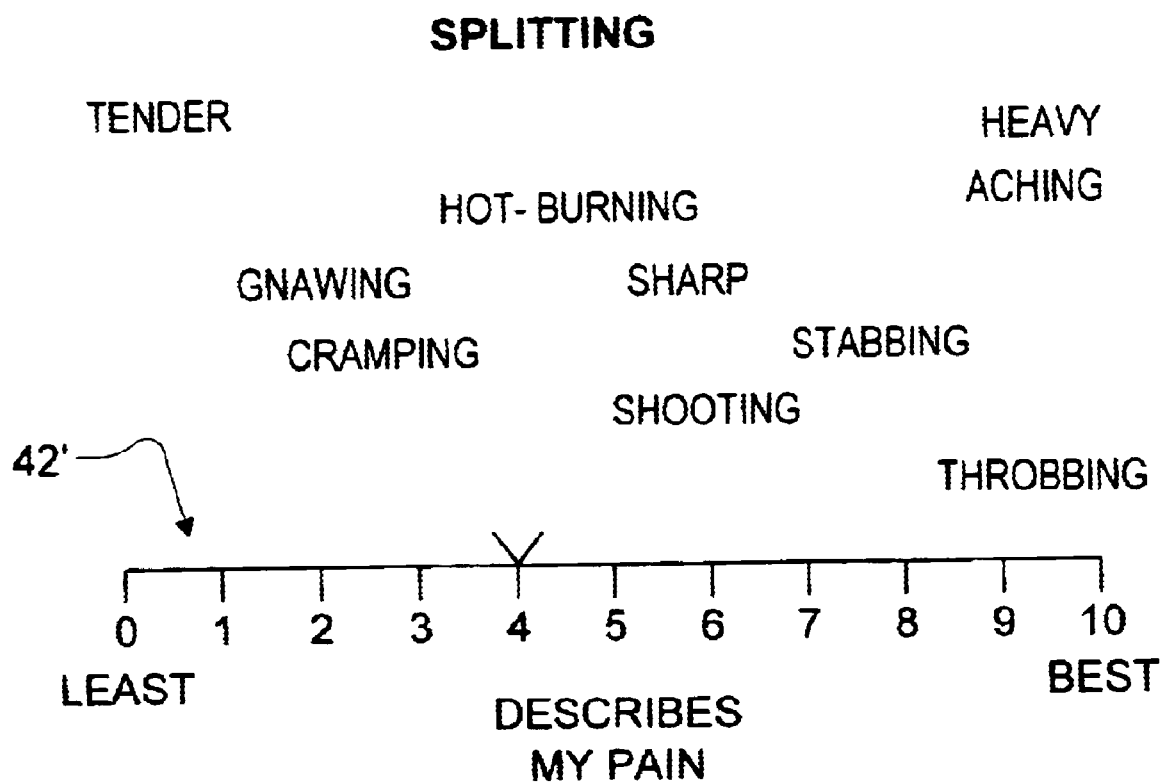
FIG. 15 is a graphical illustration of a horizontal rating scale with each of the words in a different row, according to yet another embodiment of the present invention.

When a concept representation is manipulated, an indication is preferably displayed on the rating scale indicating the user input rating. For example, the movement of a single word along the scale 42 leads to a corresponding change in the position of an arrowhead 46 that slides along the scale 42 and points to the exact rating at each instant in time. The words can appear at any position along the dimension of the computer screen that is orthogonal to the orientation of the measurement scale 42, thus allowing different items to receive the same ratings. For example, the words can be located in separate rows above the horizontal scale 42', as shown in FIG. 15, so that more than one concept can be given the same rating without the words overlapping. In the case of a vertical scale, the words can be located adjacent to each other, within the limits of the screen size.

As additional words are added to the scale 42, the user rates the words with respect to the scale and relative to the other words already rated. The method allows the user to continue manipulating the positions of the words until the user is satisfied with all the ratings. The user input information recorded includes each move, the order for each move, and the time required for each move. In one example, the user input information is stored as an animated graphical representation, which can be replayed to visualize the exact process of making each judgment.

Figure 8:
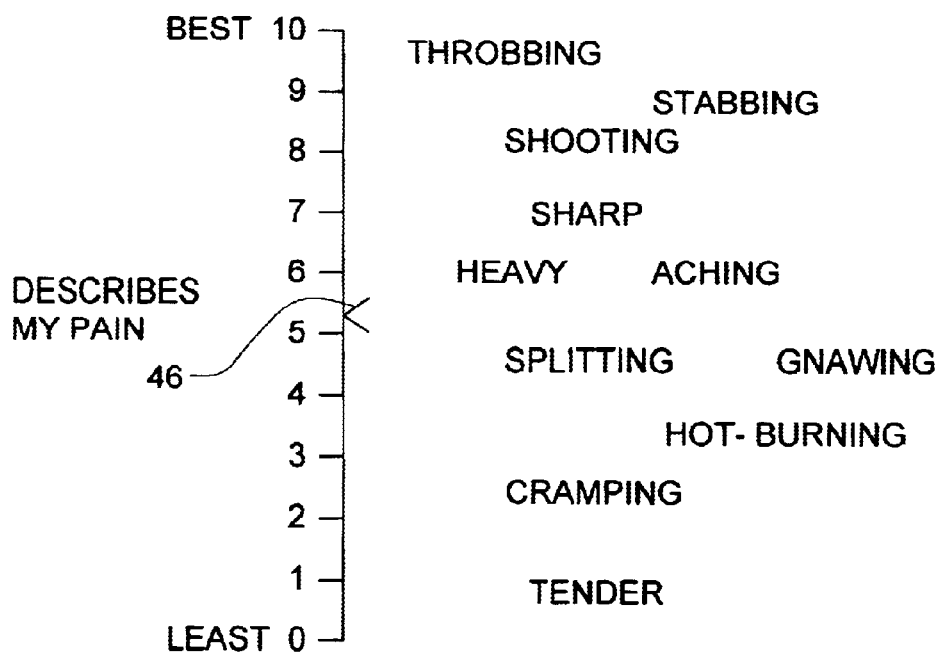
FIG. 8 is a graphical illustration of the vertical rating scale shown in FIG. 7 with the concept representations positioned relative to one another and rated based on the location relative to the rating scale.
Figure 9:
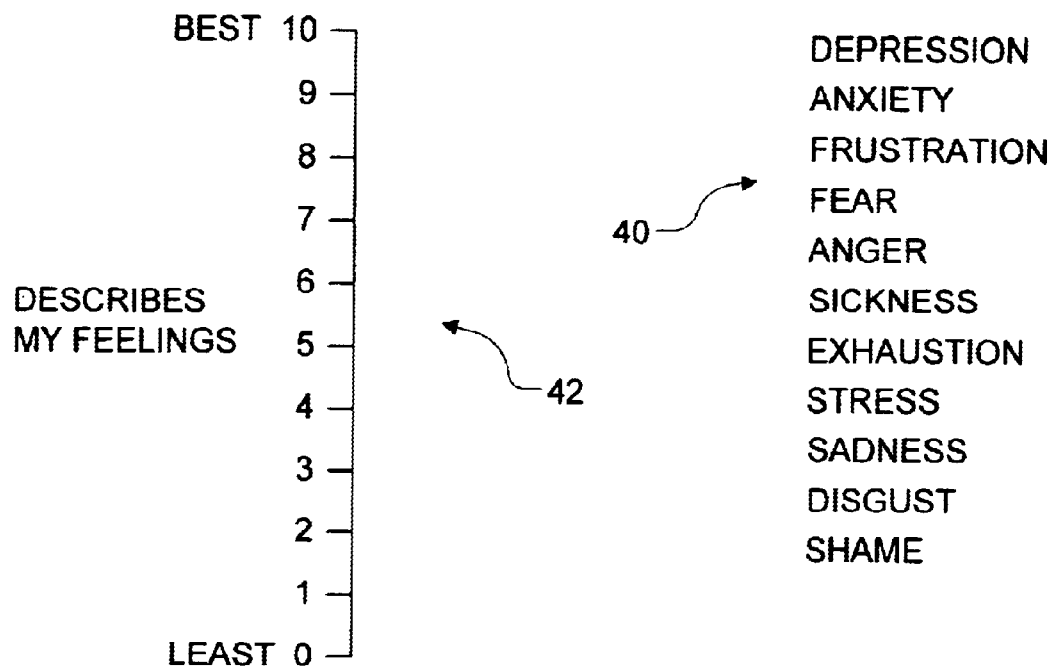
FIGS. 9 and 10 are graphical illustrations showing a vertical scale with concept representations corresponding to emotional feelings, according to another example.
Figure 10:
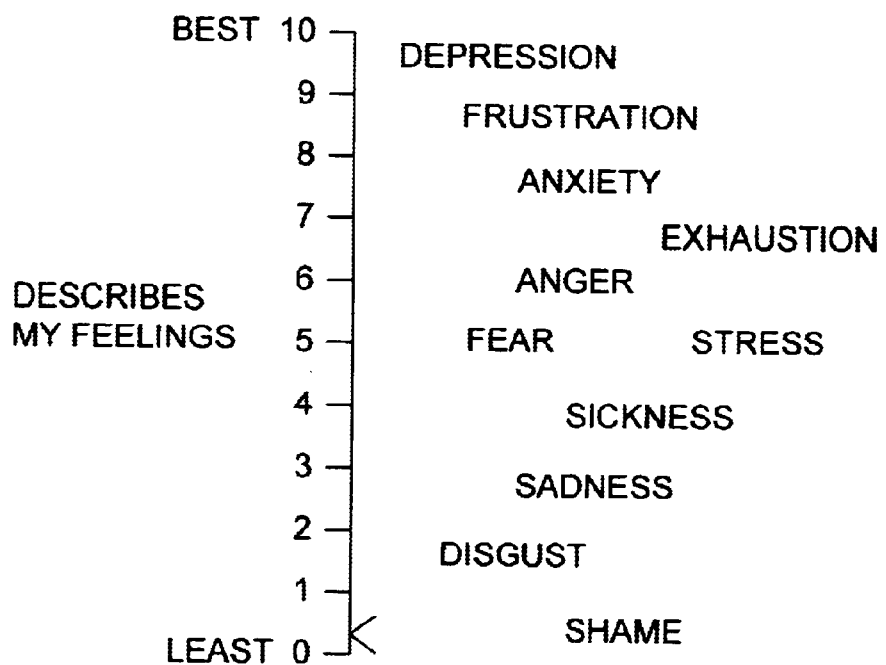
Figure 11:
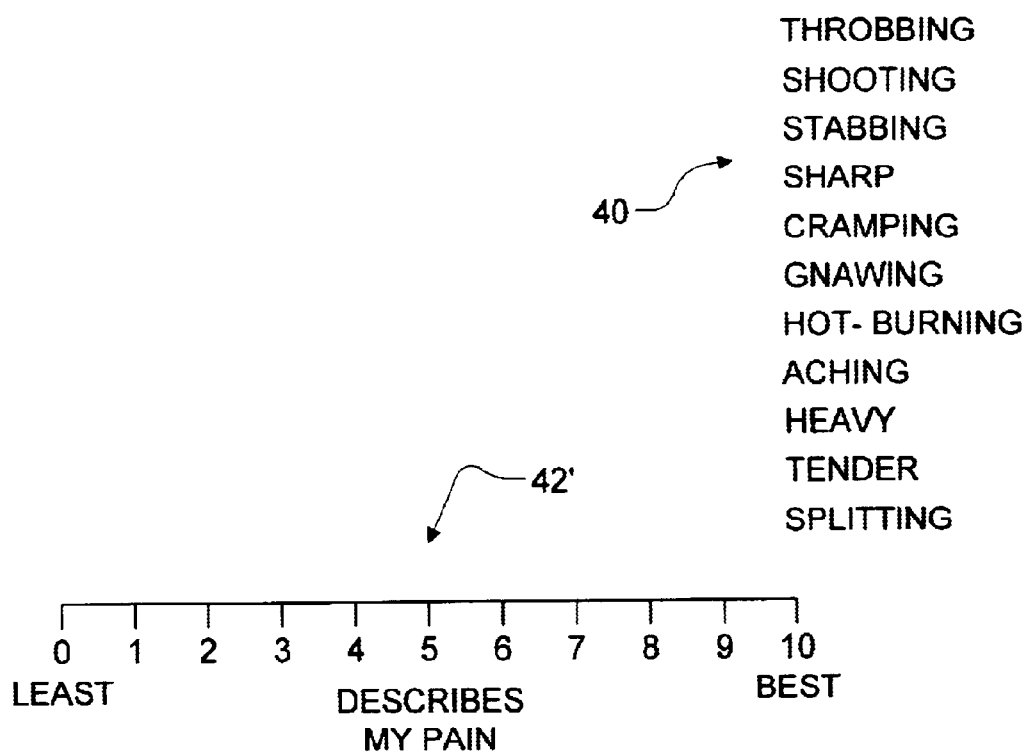
FIGS. 11–14 are graphical illustrations showing a horizontal rating scale with concept representations, according to further examples.
Figure 12:
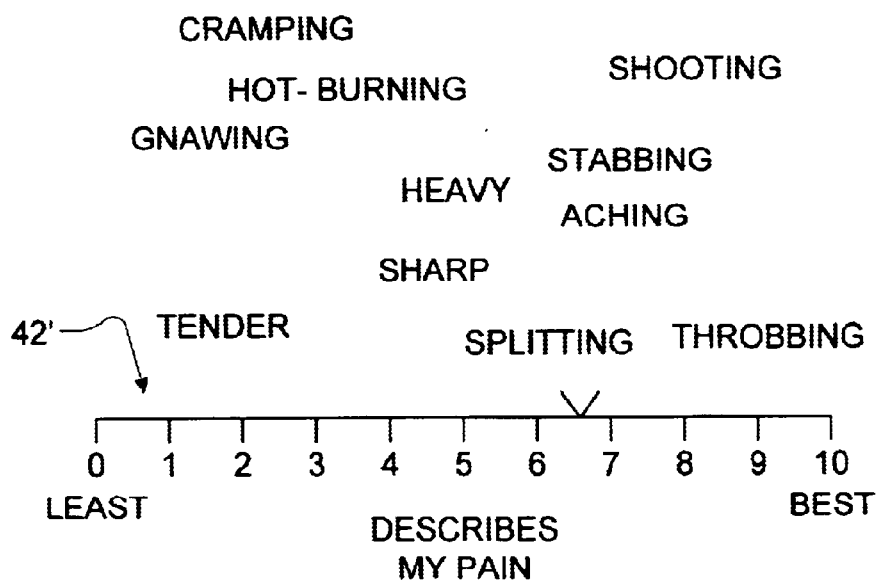
Figure 13:
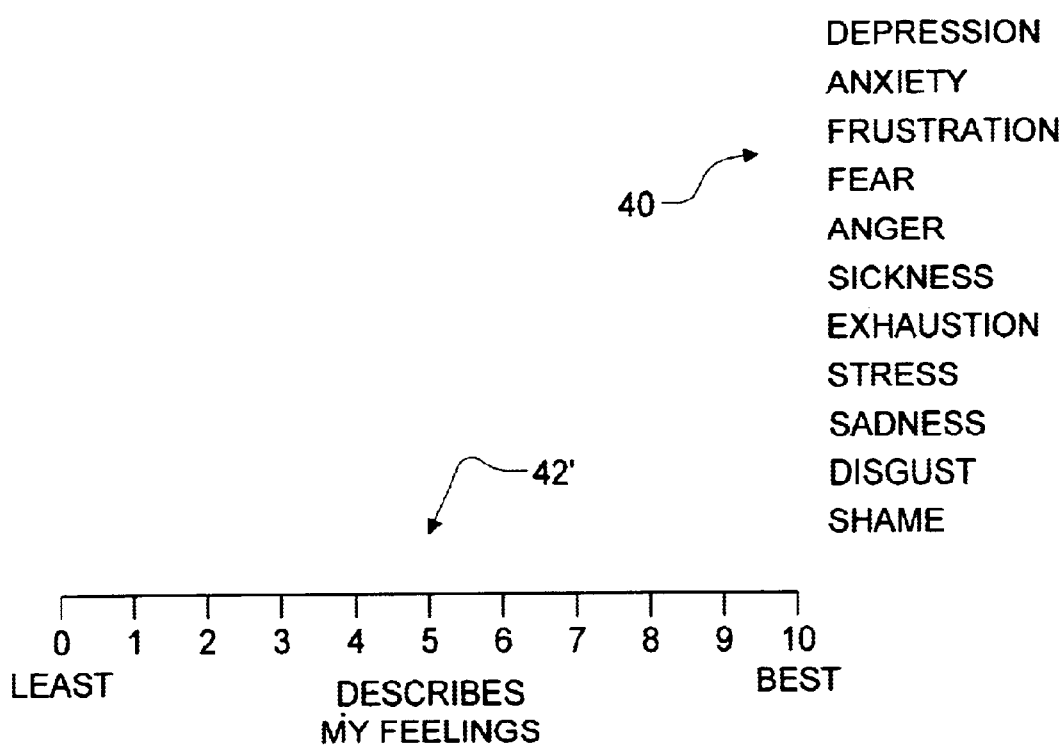
Figure 14:
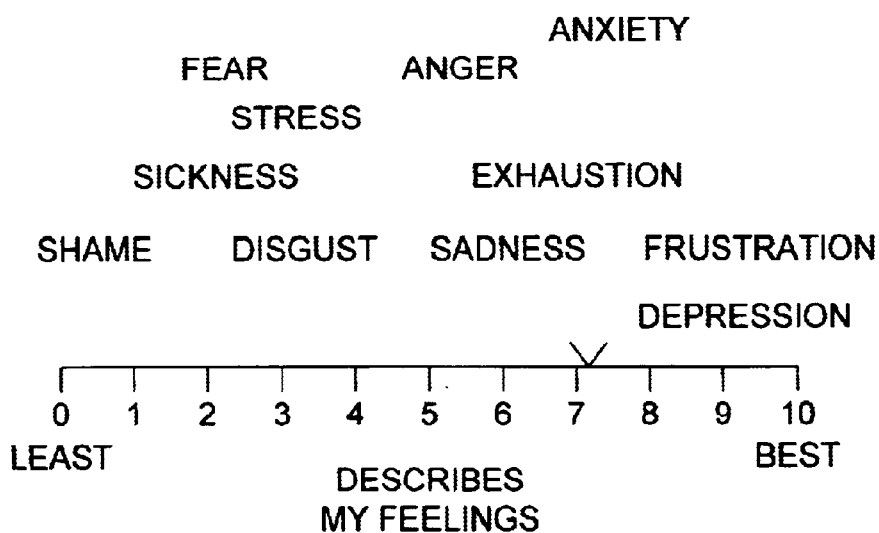

In the example illustrated in FIGS. 8 and 12, a patient in chronic pain adjusted the adjectives to indicate the appropriateness (Least to Best) of each adjective for describing the character of the patient's pain. The adjective "throbbing" was rated as the most appropriate and the adjective "tender" was rated as the least appropriate. The advantage of this method over the standard means of obtaining ratings for each adjective in isolation is that judgments are made within a "context" of other adjectives, thus encouraging the user to make distinctions among the adjectives in terms of their ratings. In the standard method when adjectives are rated in isolation in the clinic, chronic pain patients tend to choose high ratings of appropriateness or intensity for all the adjectives. In another example illustrated in FIGS. 10 and 14, the patient used the adjectives to describe the patient's feelings.

Figure 16:
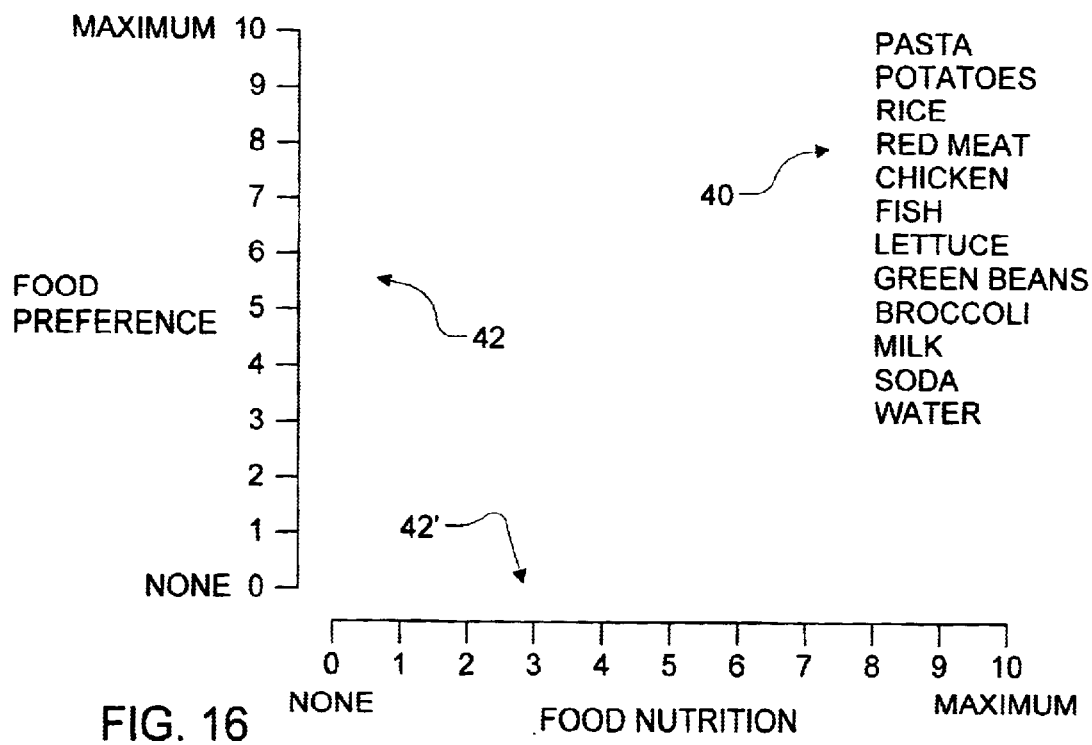
FIGS. 16–17 are graphical illustrations of a two dimensional scale with concept representations, according to yet another example.
Figure 17:
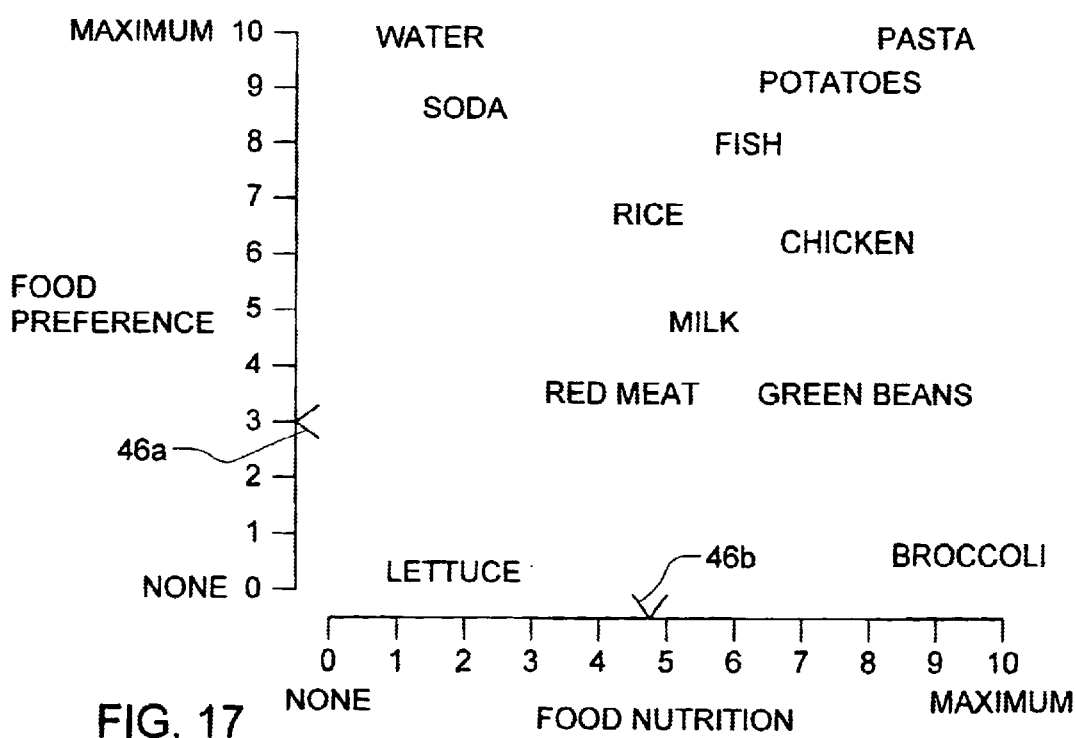

According to another example, shown in FIGS. 16–17, concept representations are located by the user along two dimensions simultaneously. As shown by example in FIG. 16, words initially appear in a vertical list 40 on the screen and a two-dimensional, orthogonal coordinate system (e.g., vertical rating scale 42 and horizontal rating scale 42') is shown with tick marks and integers designating different levels of the attribute being judged. The user moves the words (i.e., concept representations) to positions within the two-dimensional space relative to the vertical scale 42 and the horizontal scale 42'. This movement of the representation is linked in a linear fashion to movement of one arrowhead 46a along the vertical scale 42 and of another arrowhead 46b along the horizontal scale 42'. The system allows the user to continue manipulating the positions of the items in two dimensions until they are satisfied with all the ratings along both scales 42, 42'. The system records the concept ratings and movements on both scales 42, 42', the order for each move, and the time required for each move.

In one example, the user may not assign exactly the same ratings (x and y coordinates) for two or more items because this requires that the two words be placed on top of each other, thereby making them unreadable. According to another example, a three-dimensional scale can be used with each of the words located and movable in its own plane above the ground plane including the two-dimensional scale. When each of the words is moved, the x, y location is displayed on the ground plane relative to the two-dimensional scale. This three-dimensional example allows multiple words to have the same rating (i.e., the same x, y location) without the words having to be placed on top of one another.

In the example illustrated in FIG. 17, a hypothetical user expressed their preference (vertical scale) and perceived nutritional value (horizontal scale) of different foods. The item "pasta" was rated as well liked and of high nutrition; the item "water" was rated as well liked and low in nutrition; the item "broccoli" was rated as poorly liked and high in nutrition; and the item "lettuce" was rated as poorly liked and low in nutrition.

Figure 18:
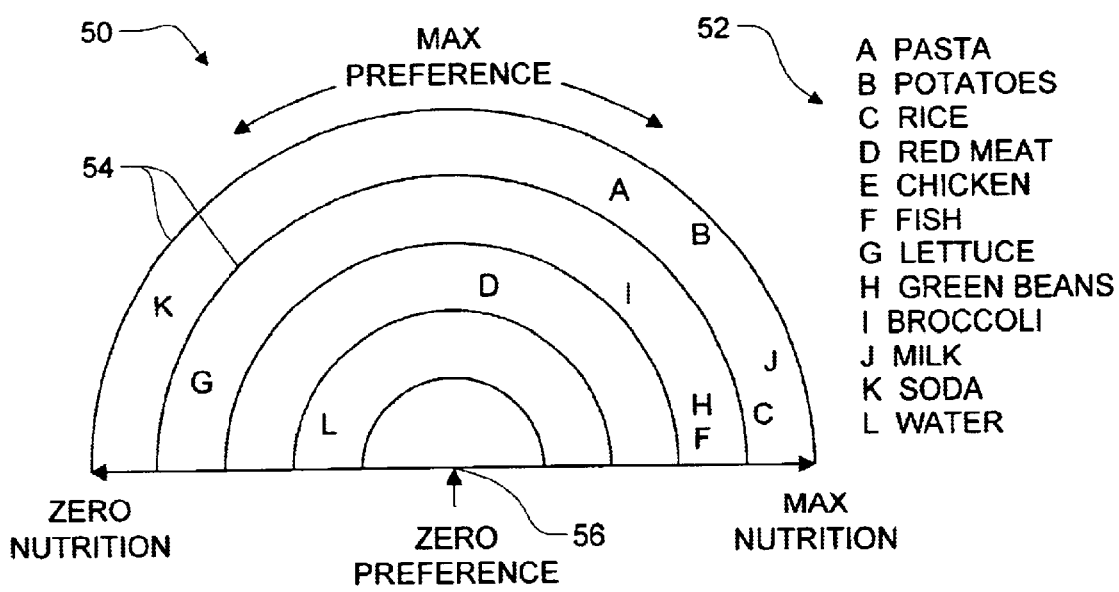
FIG. 18 is a graphical illustration of a two dimensional polar coordinate scale with concept representations, according to yet another example.

Alternatively, the two dimensional scale can be represented as a polar coordinate system 50, as shown in FIG. 18. The user moves the concept representations 52 (e.g., words, letters, pictures or icons) within one or more circles 54 to different locations in the space. The value measured along one dimension (e.g., preference) is the distance of the item from the center 56 of the circle(s) 54. The value along the second dimension (e.g., nutritional value) is the angle of a vector extending from the center 56 of the circle(s) 54.

Figure 19:
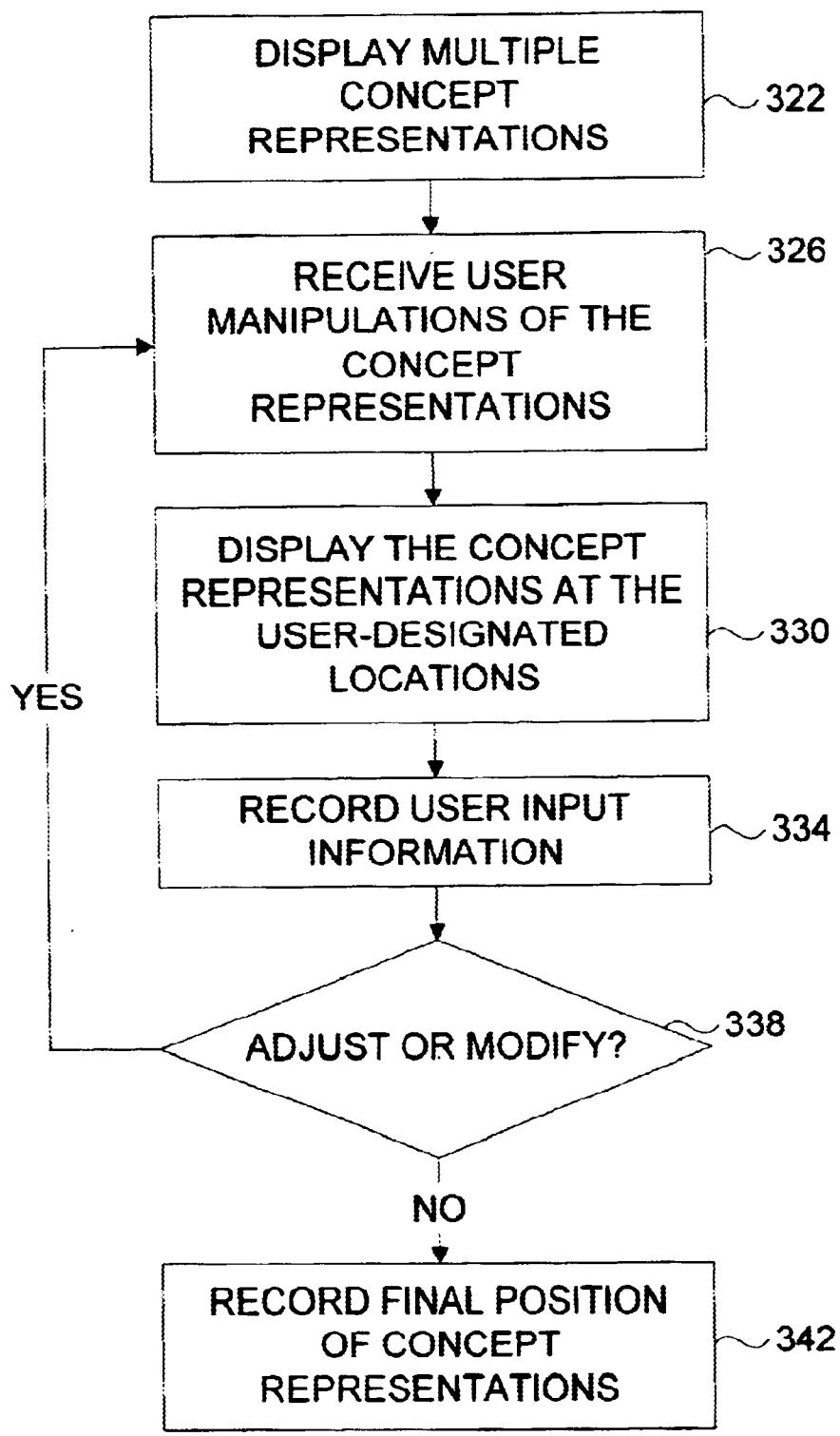
FIG. 19 is a flow chart illustrating a method for representing and recording judgments by associating concept representations in space, according to a further embodiment of the present invention.

According to another method of representing and recording judgments, as shown in FIG. 19, concept representations are positioned relative to one another in two dimensions without any physical context or rating scale. Multiple concept representations (e.g., words, pictures, or icons) are displayed, step 322. The user is asked to make judgments by manipulating the concept representations and moving the concept representations in relation to one another. The user manipulations of the concept representations are received, step 326, and the concept representations are displayed at the user-designated location, step 330. User input information is recorded as each concept representation is manipulated, step 334. These steps can be repeated to adjust or modify the user's judgment, step 338. When the user is finished, the final positions of the concept representations representing the user's judgments are recorded, step 342.

One example of this method of positioning concept representations 60 in two-dimensional space is used with food items, as shown in FIG. 20. The user locates the food items in two dimensions on the computer screen by moving words to positions relative to each other. No scales or units of measure are shown and the user is not told what the two dimensions of the screen represent. The user is instructed to adjust the items such that those items that go together (specific attributes can be specified) are close together in space and those items that do not go together are far apart in space. The inter-item distances can later be analyzed so that items are placed in either clustered groupings (non metric) or in a two-dimensional coordinate system (metric). The advantage of this method over previous manual and computer applications is that one can store a running record of every keystroke made by the user in rendering judgments as items are moved about the screen.

According to further embodiments of the present invention, any of the methods described above can incorporate the fixed resource technique, as described in greater detail in co-pending provisional application Serial No. 60/270,854 (Attorney Docket No. BAIRD-001PR) and application Ser. No. 09/950,126 (Attorney Docket No. BAIRD-001XX), both of which are incorporated herein by reference. For example, a horizontal scale 42' (for example, as shown in FIG. 15) can be used with each word (or other type of concept representation) located in its own row above the scale 42'. As one word is moved horizontally in relation to the scale 42', one or more of the other words are able to move automatically without interfering with one another in accordance with the fixed resource technique. The three-dimensional scale described above can also be used according to this embodiment to provide the fixed resources in two dimensions.

Accordingly, the system and method of the present invention is able to dynamically represent relative judgments while also recording the judgment process. Modifications and substitutions by one of ordinary skill in the art are considered to be within the scope of the present invention, which is not to be limited except by the following claims.

The invention claimed is:

1. A computerized method of representing and recording judgments of a user in relation to a rating scale, said method comprising:

displaying multiple concept representations to the user, wherein each of said concept representations represents a concept about which the user is asked to make a judgment;

displaying at least one rating scale, wherein said rating scale provides a range of possible judgments applicable to said concepts;

receiving user manipulations of selected concept representations locating said concept representations relative to said rating scale and relative to other concept representations, thereby providing user input ratings of selected concepts;

displaying said selected concept representations relative to said rating scale and relative to said other concept representations in accordance with said user input ratings; and recording at least a final location of said concept representations relative to said rating scale to provide a final judgment to be evaluated.

2. The method of claim 1 further including displaying an indication on said rating scale of said user input rating of a concept representation when said concept representation is being manipulated by the user.

3. The method of claim 1 wherein said at least one rating scale is two-dimensional including a horizontal rating scale and a vertical rating scale, for representing two different types of judgments.

4. The method of claim 1 wherein said at least one scale is represented as a two-dimensional polar coordinate system, for representing two different types of judgments.

5. The method of claim 1 wherein said concept representations are words.

6. The method of claim 1 wherein said rating scale includes numerical values for indicating said user input ratings.

7. The method of claim 1 further including continuously recording user input information as the user manipulates said concept representations, wherein said user input information allows an evaluation of a judgment making process of the user.

8. The method of claim 7 further including replaying said judgment making process of the user based upon said user input information.

9. The method of claim 1 further including dynamically adjusting a location of at least one other concept representation relative to said rating scale when each said selected concept representation is located relative to said rating scale such that a user can observe dynamically how a judgment with respect to one concept representation affects a judgment with respect to another concept representation.

10. The method of claim 9 wherein said concept representations are dynamically adjusted according to a fixed resource technique such that a sum of user input ratings for each of said selected concepts remains constant.

11. The method of claim 9 wherein said concept representations are positioned relative to said rating scale such that said concept representations can be dynamically adjusted without interfering with other said concept representations.

12. The method of claim 1 wherein said concepts include sensory symptoms, and wherein said judgment of the user is based on a degree to which the user experiences said sensory symptoms.

13. A computer program product, stored on a storage medium, for representing and recording judgments of a user in relation to a rating scale, said computer program product comprising:

code for displaying multiple concept representations to the user, wherein each of said concept representations represents a concept about which the user is asked to make a judgment;

code for displaying at least one rating scale, wherein said rating scale provides a range of possible judgments applicable to said concepts;

code for receiving user manipulations of selected concept representations locating said concept representations relative to said rating scale and relative to other concept representations, thereby providing user input ratings of selected concepts;

code for displaying said selected concept representations relative to said rating scale and relative to said other concept representations in accordance with said user input ratings; and code for recording at least a final location of said concept representations relative to said rating scale to provide a final judgment to be evaluated.

* * * * *